United States Patent [19]

Kumazawa et al.

[11] Patent Number: 5,468,869

[45] Date of Patent: Nov. 21, 1995

[54] PROCESS FOR PRODUCTION OF (AZOLYLMETHYL)-(BIPHENYLMETHYL) CYCLOPENTANOL DERIVATIVES

[75] Inventors: Satoru Kumazawa, Iwaki; Hiroyuki Enari, Tokyo, both of Japan

[73] Assignee: Kureha Kagaku Kogyo K.K., Tokyo, Japan

[21] Appl. No.: 124,763

[22] Filed: Sep. 22, 1993

[30] Foreign Application Priority Data

Sep. 24, 1992 [JP] Japan .................................. 4-277719

[51] Int. Cl.⁶ ........................ C07D 249/08; C07D 233/60
[52] U.S. Cl. ........................... 548/267.8; 548/341.1
[58] Field of Search ........................... 548/267.8, 341.1

[56] References Cited

U.S. PATENT DOCUMENTS 4,863,505  9/1989  Kumazawa et al. .................. 71/92
4,938,792  7/1990  Kumazawa et al. .................. 71/92

FOREIGN PATENT DOCUMENTS

0329397A1  8/1989  European Pat. Off. .

OTHER PUBLICATIONS

"Photolysis of Iodoaromatic Compounds in Benzene", The Journal of Organic Chemistry, vol. 30, No. 8, Aug. 12, 1965, pp. 2493–2498. Wolf et al.

Robinson, "Photochemical Reactions of, etc" J Chem Soc, 1971, 3363.

Kojima et al, "Photolysis of Chlorobenzene, etc" Chemistry Letters, 1981, pp. 1539–1540.

*Primary Examiner*—Patricia L. Morris
*Attorney, Agent, or Firm*—Lowe, Price, LeBlanc & Becker

[57] ABSTRACT

This invention provides a simple process for production of an (azolylmethyl)(biphenylmethyl)cyclopentanol derivative represented by the following formula (I) in a good yield. This process comprises, as described in the following reaction formula, reacting an (azolylmethyl)(halogenophenylmethyl)cyclopentanol derivative represented by the following formula (II) with a benzene derivative represented by the following formula (III) by light irradiation.

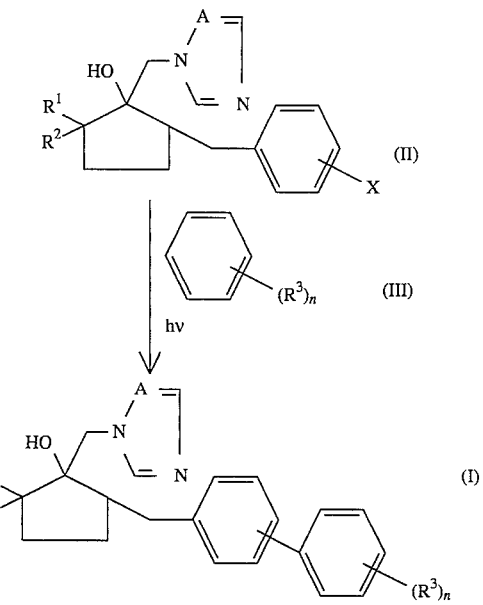

wherein X denotes a halogen atom, $R^1$ and $R^2$ denote independently a hydrogen atom or a C1–C5 alkyl group, $R^3$ denotes a C1–C5 alkyl group, n means an integer of 0–2, and A represents CH or N.

1 Claim, No Drawings

PROCESS FOR PRODUCTION OF (AZOLYLMETHYL)-(BIPHENYLMETHYL) CYCLOPENTANOL DERIVATIVES

BACKGROUND OF THE INVENTION

1) Field of the Invention

The present invention relates to a process for production of (azolylmethyl)(biphenylmethyl)cyclopentanol derivatives capable of utilizing as an effective ingredient of agricultural chemicals and medicines.

2) Description of the Related Art

U.S. Pat. No. 4,863,505 and U.S. Pat. No. 4,938,792 disclose a process for production of (azolylmethyl)(biphenylmethyl)cyclopentanol derivatives including the following compounds represented by the formulas (A) and (B).

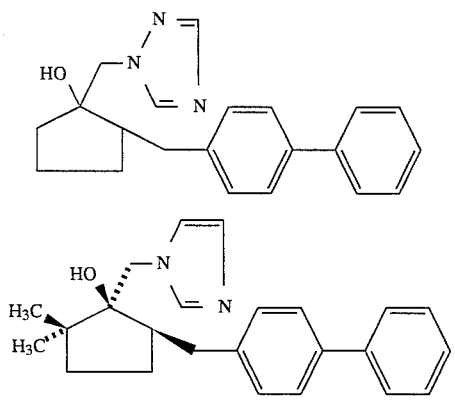

It is however unknown yet a process for production of (azolylmethyl)(biphenylmethyl)cyclopentanol derivative in which a halogen atom of (azolylmethyl)-(halogenophenylmethyl)cyclopentanol derivative is substituted with an unsubstituted or lower alkyl substituted benzene derivative.

SUMMARY OF THE INVENTION

Accordingly, it is an object of the present invention to provide a process for producing simply (azolylmethyl)(biphenylmethyl)cyclopentanol derivatives in a good yield.

As a result of earnest studies concerning the process for production of (azolylmethyl)(biphenylmethyl)cyclopentanol derivatives represented by the following formula (I) using as a starting material an (azolylmethyl)(halogenophenylmethyl)cyclopentanol derivative represented by the following formula (II), the present inventors have completed the present invention.

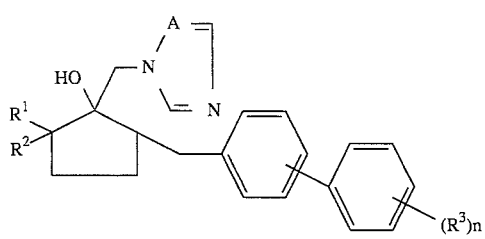

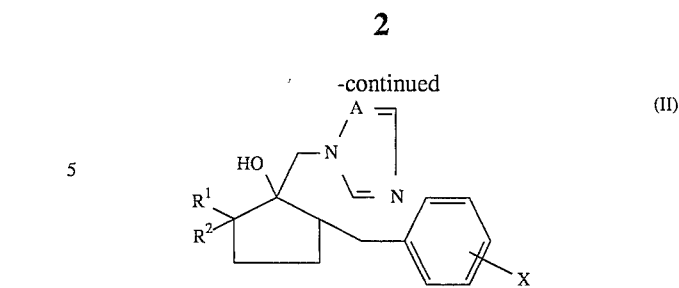

wherein X denotes a halogen atom, $R^1$ and $R^2$ denote independently a hydrogen atom or a C1–C5 alkyl group, $R^3$ denotes a C1–C5 alkyl group, n means an integer of 0–2, and A means CH or N.

Accordingly, an object of the present invention is to provide a process for production of an (azolylmethyl)(biphenylmethyl)cyclopentanol derivative represented by the formula (I) which comprises, as described in the following reaction formula (a), reacting an (azolylmethyl)(halogenophenylmethyl)cyclopentanol derivative represented by the formula (II) with a benzene derivative represented by the formula (III) by light irradiation.

[Reaction formula (a)]

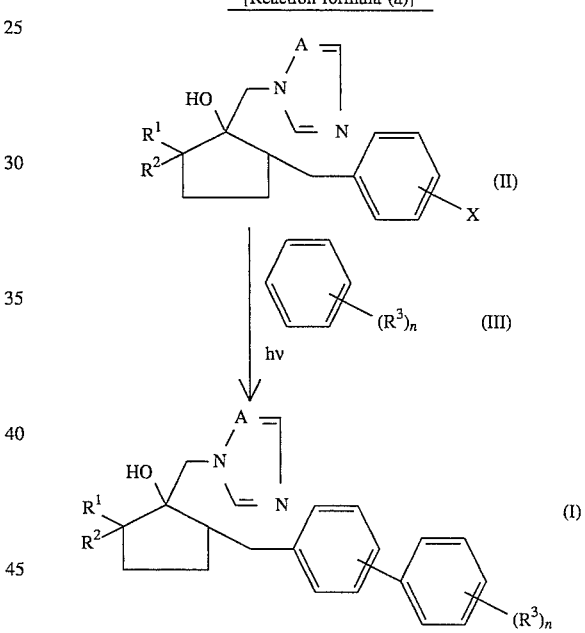

wherein X denotes a halogen atom, $R^1$ and $R^2$ denote independently a hydrogen atom or a C1–C5 alkyl group, $R^3$ denotes a C1–C5 alkyl group, n means an integer of 0–2, and A means CH or N.

DETAILED DESCRIPTION OF PREFERRED EMBODIMENTS

The (azolylmethyl) (halogenophenylmethyl) cyclopentanol derivative represented by the formula (II) as the starting material in the present invention can be prepared according to a process described in, for example, U.S. Pat. No. 4,863,505 and U.S. Pat. No. 4,938,792.

Namely, as be shown in the following reaction formula (b), 1-(halogenophenylmethyl)-2-oxocyclopentanecarboxylic acid alkyl ester derivative represented by the formula (VII) is subjected to hydrolysis-decarboxylation to obtain a 2-(halogenophenylmethyl)cyclopentanone derivative represented by the formula (VI). (This step is referred to as "hydrolysis-decarboxylation", hereinafter.)

[Reaction formula (b)]

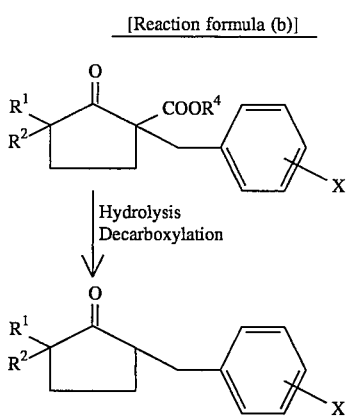

wherein X, $R^1$ and $R^2$ have the same meanings as defined above, and $R^4$ means a C1–C4 alkyl group.

Next, as be shown in the following reaction formula (c), the compound represented by the formula (VI) is allowed to react with dimethyloxosulfonium methylide of dimethylsulfonium methylide to obtain an oxaspiroheptane derivative represented by the formula (V). (This step is referred to as "epoxidation", hereinafter.)

The resultant compound represented by the formula (V) is allowed to react with an azole compound represented by the formula (IV) to obtain the (azolylmethyl)(halogenophenylmethyl)cyclopentanol derivative represented by the formula (II) which is a starting material of this invention. (This step is referred to as "azolation", hereinafter.)

[Reaction formula (c)]

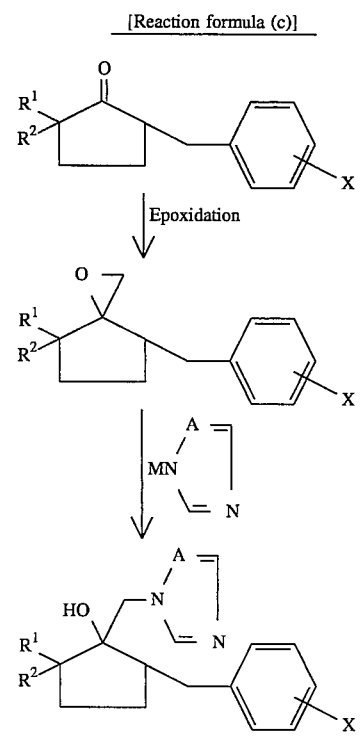

wherein X, $R^1$ $R^2$ and A have the same meanings as defined above, and M is a hydrogen atom or an alkali metal atom.

Next, as described in the above reaction formula (a), the (azolylmethyl)(biphenylmethyl)cyclopentanol derivative represented by the formula (I) of this invention can be produced simply in a high yield from the (azolylmethyl)(halogenophenylmethyl)cyclopentanol derivative represented by the formula (II) as a starting material by substituting a halogen atom of the halogenophenylmethyl group with a benzene derivative represented by the formula (III) by light irradiation. (This step is referred to as "phenylation", hereinafter.)

Examples of $R^1$ and $R^2$ in the above described compounds include hydrogen atom, methyl group, ethyl group, n-propyl group, i-propyl group, n-butyl group, i-butyl group and n-pentyl group. Examples of $R^3$ in the above described compounds include hydrogen atom, methyl group, ethyl group, n-propyl group, i-propyl group, n-butyl group, i-butyl group, t-butyl group and n-pentyl group.

Examples of a diluent using in a series of reactions of the process for producing the (azolylmethyl)(biphenylmethyl)cyclopentanol derivative represented by the formula (I) of this invention include the following.

Hydrocarbons such as benzene, toluene, xylene, hexane and the like.

Halogenated hydrocarbons such as methylene chloride, chloroform, carbon tetrachloride and the like.

Alcohols such as methanol, ethanol, isopropanol, t-butanol and the like.

Ethers such as diethyl ether, diisopropyl ether, tetrahydrofuran, dioxane and the like.

Acetonitrile, acetone, dimethylformamide, dimethylacetamide, 1-methyl-2-pyrrolidinone and dimethylsulfoxide, etc.

In additon, the reactions may be carried out in the presence of a base together with the above diluent. Such base used in this invention include the following.

Carbonates such as sodium carbonate and potassium carbonate, etc.

Hydroxides such as sodium hydroxide and potassium hydroxide, etc.

Alkali metal alkoxides such as sodium methoxide, sodium ethoxide and potassium t-butoxide, etc.

Alkali metal hydrides such as sodium hydride and potassium hydride, etc.

Organometal compounds of alkali, such as n-buthyllithium, etc.

Organic tertiary amines such as triethylamine and pyridine, etc.

Examples of acids include inorganic acids such as hydrochloric acid, hydrobromic acid, hydroiodic acid, sulfuric acid etc. and organic acids such as formic acid, acetic acid, butyric acid and p-toluenesulfonic acid, etc.

Hydrolysis-decarboxylation 1-(Halogenophenylmethyl)-2-oxocyclopentanecarboxylic acid alkyl ester derivative represented by the formula (VII) is subjected to hydrolysis-decarboxylation to easily convert into the 2-(halogenophenylmethyl)cyclopentanone derivative represented by the formula (VI) in a high yield.

The hydrolysis-decarboxylation may be carried out under any of acidic condition and basic condition.

When the reaction is carried out under an acidic condition, it is preferred to use acetic acid as a solvent in addition to water, and an inorganic acid such as hydrochloric acid or hydrobromic acid, etc. is used as a catalyst.

The reaction temperature in this reaction is in a range of from 50° C. to a refluxing temperature, and preferably from 80° C. to the refluxing temperature of the system.

When the reaction is carried out under a basic condition, it is preferred to use a lower alcohol or an aromatic hydrocarbon in addition to water.

As the base, an alkali metal base, preferably sodium hydroxide or potassium hydroxide is used in this reaction.

The reaction temperature of this reaction is in a range of from 50° C. to the refluxing temperature of the system, preferably from 80° C. to the refluxing temperature.

The reaction period in the reaction under the acidic or basic condition is in a range of from 2 to 24 hours, and the reaction is more preferred to carried out under stirring.

Epoxidation

The oxaspiroheptane derivative represented by the formula (V) can be produced from the compound represented by the formula (VI) according to the process disclosed in, for example, Organic Synthesis (Org. Synth.) 49, 78(1969) and Journal of American Chemical Society (J. Am. Chem. Soc.) 1965, 1353.

It is preferred to react the compound represented by the formula (VI) with dimethyloxosulfonium methylide or dimethyl sulfonium methylide which is prepared by reacting trimethylsulfoxonium iodide or trimethylsulfonium iodide with a base (for example, sodium hydride), in the above diluent (dimethylsulfoxide is particularly preferred.).

The dimethyloxosulfonium methylide or dimethylsulfonium methylide is preferably used in an amount of from 1.0 to 2.0 equivalents to the compound represented by the formula (VI). The reaction temperature in this case is preferred in a range of from 25 to 100° C., and the reaction period is preferred in a range of from 1 to 40 hours.

After conclusion of the above described reaction, the reaction mixture is cooled and extracted with an organic solvent such as ethyl acetate, chloroform, methylene chloride, benzene or hexane, etc. in iced water to separate an organic layer. After the separated organic layer is washed with water and dried, the solvent is distilled away under a reduced pressure. The resultant residue is then purified to obtain the title compound represented by the formula (V). The purification can be carried out by recrystallization or by chromatography on a silica gel column.

Thus resultant oxaspiroheptane derivative represented by the formula (V) includes two kinds of stereoisomeric structure, namely, cis type and trans type, based on the configuration of the oxygen atom in 1-position and the halogenophenylmethyl group in 4-position of the 1-oxaspiro [2.4]heptane ring thereof.

Separation of these stereoisomers can be carried out, for example, by chromatography (thin-layer, column or high performance liquid chromatography, etc.).

The stereoisomeric structure of them can be ascertained by, for example, NMR spectra.

Azolation

In order to prepare the (azolylmethyl)(halogenophenylmethyl)cyclopentanol derivative represented by the formula (II) as the starting material of this invention, the oxaspiroheptane derivative represented by the formula (V) may be added in an amount of 0.5–1.0 equivalent to a solution of the azole compound represented by the formula (IV) in the above described diluent in a presence of, if necessary, the above described base. Alternatively, the azole compound represented by the formula (IV) may be added to a solution of the compound represented by the formula (V) in the diluent to react in a presence of a base.

The reaction temperature in this reaction may be suitably adopted in a range of from the solidifying point of the diluent to the boiling point thereof, but it is preferred to react at a temperature in a range of from 0° to 120° C., preferably 60°–120° C.

The reaction period of time is in a range of from 1 to 10 hours, and it is preferred to react with stirring.

The (azolylmethyl) (halogenophenylmethyl) cyclopentanol derivative represented by the formula (II) includes two kinds of stereoisomers, namely, cis type and trans type originated in isomers of the compound represented by the formula (V).

Further, it includes optical isomers originated in 1-position, 2-position and 5-position of the cyclopentane ring.

Phenylation

In order to produce the (azolylmethyl)(biphenylmethyl) cyclopentanol derivative represented by the formula (I) according to the present invention, the compound represented by the formula (II) is dissolved in the compound represented by the formula (III) which is used as a diluent (if necessary, the above described diluent may be used). The mixture is allowed to react by light irradiation.

The reaction temperature in this reaction may be suitably adopted in a range of from the solidifying point of the diluent to the boiling point thereof, but it is preferred to react at a temperature in a range of from –20 to 120° C., preferably 60°–120° C.

The reaction period is in a range of from 0.5 to 10 hours, and it is preferred to react with stirring.

As a light source, a high pressure mercury lamp or a low pressure mercury lamp of 100–400 W may be used. The reaction is carried out by light irradiation having a wavelength of from 280 to 660 nm, preferably from 310 to 590 nm.

The (azolylmethyl) (biphenylmethyl) cyclopentanol derivative represented by the formula (I) includes two kinds of stereoisomers, namely, cis type and trans type originated in isomers of the compound represented by the formula (II).

Further, it includes optical isomers originated in 1-position, 2-position and 5-position of the cyclopentane ring.

In the process for production of the compound (I) by the phenylation of the present invention, it is possible to produce all of these isomers and mixtures of them in a suitable ratio.

According to the present invention, the (azolylmethyl)(biphenylmethyl)cyclopentanol derivatives represented by the above formula (I) can be produced simply in a good yield, because the halogen atom of the halogenophenylmethyl group of the (azolylmethyl)(halogenophenylmethyl)cyclopentanol derivative represneted by the above formula (II) is substituted by a benzene derivative represented by the above formula (III) under light irradiation.

EXAMPLES

In the following, the present invention will be illustrated in greater detail with reference to preparation examples. The present invention however should not be restricted thereto unless the preparation examples deviate from the scope and the spirits of the present invention.

PREPARATION EXAMPLE 1

Production of cis-5-isopropyl-cis-2-(4-phenylbenzyl)-1-(1H-1,2,4-triazol-1-ylmethyl)-1-cyclopentanol cis-2-(4-Chlorobenzyl)-cis-5-isopropyl-1 -(1H-1,2,4-triazol-1-ylmethyl)-1-cyclopentanol (504.5 mg) was dissolved in 250 ml of benzene, and the resultant solution was irradiated for 6 hours with ultraviolet light of a high pressure mercury lamp (output: 400 W, wavelength range: 365–430 nm) by means of ultraviolet light generation reactor (high pressure Type UV-HT: produced by Ishii Shoten Kabushiki Kaisha) while cooling with ice under stirring. The reaction solution was then evaporated to obtain 756 mg of a reddish brown oily product. The resultant oil was purified by chromatography on a silica gel column to produce 330 mg of the title compound.

Light yellow crystal, melting point: 130.0°–104.4° C. NMR Spectrum (250 MHz-$^1$H-NMR, CDCl$_3$, δ ppm 0.96(d, 3H, J=6.7 Hz) 0.99(d, 3H, J=6.7 Hz) 1.35–1.80(m, 6H) 1.93–2.12-(m, 1H) 2.35(s-like, 1H) 2.37(d, 1H, J-3.7 Hz) 2.77(s, 1H) 4.24(d, 1H, J=14.0 Hz) 4.39(d, 1H, J-14.0 Hz) 7.14(d, 2H, J--8.5 Hz) 7.44(d, 2H, J=8.5 Hz) 7.20–7.62(m, 5H) 7.99(s, 1H) 8.13(s, 1H)

PREPARATION EXAMPLE 2

Production of 2,2-dimethyl-1-(1H-imidazol-1-ylmethyl)-cis-5-(4-phenylbenzyl)-1-cyclopentanol cis-5-(4-Chlorobenzyl)-2,2-dimethyl-1-(1 H-imidazol-1-ylmethyl)-1-cyclopentanol (500 mg) was dissolved in 250 ml of benzene, and the resultant solution was irradiated for 5 hours with ultraviolet light of a high pressure mercury lamp (output: 400 W, wavelength range: 365–430 nm) by means of ultraviolet light generation reactor (high pressure Type UV-HT: produced by Ishii Shoten Kabushiki Kaisha) while cooling with ice under stirring. A reddish brown oily product obtained by evaporating the reaction solution was purified by chromatography on a silica gel column to produce 350 mg of the title compound.

Melting point: 162°–163° C. NMR spectrum < 1H-NMR, CDCl$_3$, δ ppm) 0.80(s, 3H) 1.03(s, 3H) 1.12–2.08(m, 4H) 2.37(bs, 3H) 2.43(s, 1H) 4.00(s, 2H) 6.88–7.78(m, 12H)

PREPARATION EXAMPLE 3

Production of 2-(4-phenylbenzyl)-1-(1H-1,2,4-triazol-1-ylmethyl)-1-cyclopentanol 2-(4-Chlorobenzyl)-1-(1H-1,2,4-triazol-1 -ylmethyl)-1-cyclopentanol (500 mg) was dissolved in 250 ml of benzene, and the resultant solution was irradiated for 5 hours with ultraviolet light of a high pressure mercury lamp (output: 400 W, wavelength range: 365–430 nm) by means of ultraviolet light generation reactor (high pressure Type UV-HT: produced by Ishii Shoten Kabushiki Kaisha) while cooling with ice under stirring. A reddish brown oily product obtained by evaporating the reaction solution was purified by chromatography on a silica gel column to produce 335 mg of the title compound.

Melting point: 146°–147° C.

What is claimed is:

1. A process for the production of an (azolylmethyl) (4-phenylbenzyl)cyclopentanol derivative represented; by the following formula (I):

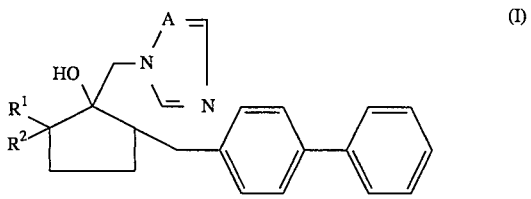

wherein R$^1$ and R$^2$ denote independently a hydrogen atom or a C1–C5 alkyl group, and A represents CH or N, which comprises: reacting an (azolylmethyl) (4-chlorobenzyl) cyclopentanol derivative represented by the following formula (II):

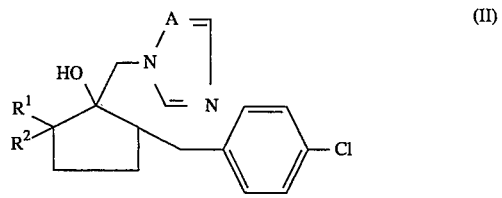

wherein R$^1$, R$^2$ and A represent each the same meaning as described above, with benzene by light irradiation.

* * * * *